(12) United States Patent
Ogata et al.

(10) Patent No.: US 11,589,734 B2
(45) Date of Patent: *Feb. 28, 2023

(54) ENDOSCOPE

(71) Applicant: PANASONIC I-PRO SENSING SOLUTIONS CO., LTD., Fukuoka (JP)

(72) Inventors: Shigeki Ogata, Fukuoka (JP); Naomi Shirai, Fukuoka (JP)

(73) Assignee: I-PRO CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/172,653

(22) Filed: Feb. 10, 2021

(65) Prior Publication Data
US 2021/0161369 A1 Jun. 3, 2021

Related U.S. Application Data

(63) Continuation of application No. 16/785,095, filed on Feb. 7, 2020, now Pat. No. 10,973,394.

(30) Foreign Application Priority Data

Mar. 14, 2019 (JP) .............................. JP2019-047222

(51) Int. Cl.
*A61B 1/005* (2006.01)
*A61B 1/00* (2006.01)
(Continued)

(52) U.S. Cl.
CPC ...... *A61B 1/00114* (2013.01); *A61B 1/00133* (2013.01); *A61B 1/045* (2013.01);
(Continued)

(58) Field of Classification Search
CPC . A61B 1/00114; A61B 1/00133; A61B 1/045; A61B 1/0676; H04N 5/2252; H04N 5/2253; H04N 5/2258
See application file for complete search history.

(56) References Cited

U.S. PATENT DOCUMENTS 7,543,376 B2 6/2009 Yoshino et al.
8,427,572 B2 4/2013 Higashiyama et al.
(Continued)

FOREIGN PATENT DOCUMENTS

JP 2010-184054 A 8/2010
JP 2011-206333 A 10/2011
(Continued)

OTHER PUBLICATIONS

Office Action issued in Japanese family member No. 2019-047222 dated Oct. 25, 2022, together with an English-language translation.

*Primary Examiner* — Patrick E Demosky
(74) *Attorney, Agent, or Firm* — Greenblum & Bernstein P.L.C.

(57) ABSTRACT

An endoscope includes a scope provided with a hard portion at a distal end of a long flexible portion having flexibility; an image capturing portion housed in the hard portion and having an image sensor; a transmission cable inserted into the scope and conductively connected to the image sensor at a distal end via a substrate, and a voltage conversion device mounted on the substrate and outputting a constant voltage to the image sensor with respect to a input voltage input to the transmission cable.

8 Claims, 14 Drawing Sheets

(51) Int. Cl.
*H04N 5/225* (2006.01)
*A61B 1/06* (2006.01)
*A61B 1/045* (2006.01)

(52) U.S. Cl.
CPC ......... *A61B 1/0676* (2013.01); *H04N 5/2252* (2013.01); *H04N 5/2253* (2013.01); *H04N 5/2258* (2013.01)

(56) References Cited

U.S. PATENT DOCUMENTS

| | | |
|---|---|---|
| 2006/0272850 A1 | 12/2006 | Morimoto et al. |
| 2009/0145651 A1 | 6/2009 | Yoshino et al. |
| 2011/0249106 A1 | 10/2011 | Makino et al. |
| 2011/0261183 A1 | 10/2011 | Ma et al. |
| 2015/0164305 A1 | 6/2015 | Kohno |
| 2018/0008124 A1 | 1/2018 | Fujimoto et al. |
| 2019/0038112 A1 | 2/2019 | Kobayashi et al. |
| 2019/0082938 A1 | 3/2019 | Okayama et al. |
| 2019/0199895 A1 | 6/2019 | Ichihara et al. |
| 2019/0201091 A1* | 7/2019 | Yates ................ A61B 18/1233 |

FOREIGN PATENT DOCUMENTS

| | | |
|---|---|---|
| JP | 2011-254525 A | 12/2011 |
| JP | 2012-064883 A | 3/2012 |
| JP | 2018-089066 A | 6/2018 |
| WO | 2016-208685 A1 | 12/2016 |
| WO | 2018-123140 A1 | 7/2018 |

\* cited by examiner

ENDOSCOPE

CROSS-REFERENCE TO RELATED APPLICATIONS

The present application is a continuation of U.S. patent application Ser. No. 16/785,095, filed Feb. 7, 2020, which claims the benefit of Japanese Patent Application No. 2019-047222, filed Mar. 14, 2019. The disclosures of both above-identified applications are expressly incorporated herein by reference in their entireties.

TECHNICAL FIELD

The present disclosure relates to an endoscope.

BACKGROUND ART

In an endoscope, a reflection signal obtained from an image sensor may be transmitted by a low voltage differential signaling (LVDS) signal from a camera head including an image sensor such as a charge coupled device (CCD) or a complementary metal oxide semiconductor (CMOS) to a camera control unit (CCU) that controls an operation of the camera head. LVDS is said to be capable of signal processing with high-speed transmission, small signal amplitude, low power consumption, and small electromagnetic interference. In a case where the LVDS signal is adopted, when a transmission cable length is long, not only a Low side voltage specification of the image capturing device itself cannot be satisfied by a voltage drop due to internal resistance of a transmission cable, a phenomenon occurs in which amplitude of a differential signal is small, frequency characteristics deteriorate, and rise time and fall time of the differential signal is long. Therefore, there is a problem that accurate information cannot be transmitted without satisfying data reproduction conditions in the CCU.

Therefore, in a camera head separated camera device disclosed in Patent Literature 1, a camera control unit includes a control means that transmits a predetermined direct current (DC) voltage to the camera head in the camera head separated camera device that connects a camera head and a camera control unit via a cable. The camera head includes an LVDS conversion driver that transmits the LVDS signal to be transmitted to the camera control unit, an LVDS control portion that controls the LVDS conversion driver portion, and a correction control portion that outputs a correction value of the LVDS signal to be supplied to the LVDS control portion. According to the camera head separated camera device, the LVDS signal can be stably transmitted from the camera head to the CCU regardless of the length of the transmission cable, and stable video can be output.

CITATION LIST

Patent Literature

Patent Literature 1: JP-A-2011-254525

SUMMARY OF INVENTION

In consideration of mounting an image capturing device such as a CMOS or the like described above on a distal end portion of medical equipment such as an endoscope, examples of a technical measure for minimizing the voltage drop (droop) at the time of power supply to the distal end portion include providing an adjustment circuit formed of a condenser, a resistor, a coil, and the like.

However, when a small diameter is required for the distal end portion like medical equipment such as an endoscope, since there is a limitation on housing space at the distal end portion, it is difficult to provide an electronic circuit such as an adjustment circuit described above or the correction control portion described in Patent Literature 1.

The present disclosure is devised in view of the above-described related circumstances, and an object thereof is to provide an endoscope that reduces an increase in diameter of a distal end portion even though a transmission cable of a video signal obtained from an image capturing portion disposed at the distal end portion is long and that stably operates the image capturing portion to obtain a high-resolution video signal.

The present disclosure provides an endoscope including a scope provided with a hard portion at a distal end of a long flexible portion having flexibility, an image capturing portion having an image sensor housed in the hard portion, a transmission cable inserted into the scope and conductively connected to the image sensor at a distal end via a substrate, and a voltage conversion device mounted on the substrate and outputting a constant voltage to the image sensor with respect to a voltage input to the transmission cable.

According to the present disclosure, in the endoscope, an increase in diameter of a distal end portion can be reduced even though a transmission cable of a video signal obtained from an image capturing portion disposed at the distal end portion is long, and the image capturing portion can be stably operated to obtain a high-resolution video signal.

DESCRIPTION OF EMBODIMENTS

Hereinafter, embodiments that specifically disclose configuration and operation of the endoscope according to the present disclosure will be described in detail with reference to the accompanying drawings. However, unnecessarily detailed description may be omitted. For example, a detailed description of an already well-known matter or a repeated description of substantially the same configuration may be omitted. This is to avoid unnecessary redundancy of the following description and to facilitate understanding of those skilled in the art. It is to be understood that the accompanying drawings and the following description are provided to enable those skilled in the art to fully understand the present disclosure, and are not intended to limit the scope of claims.

First Embodiment

Figure 1:
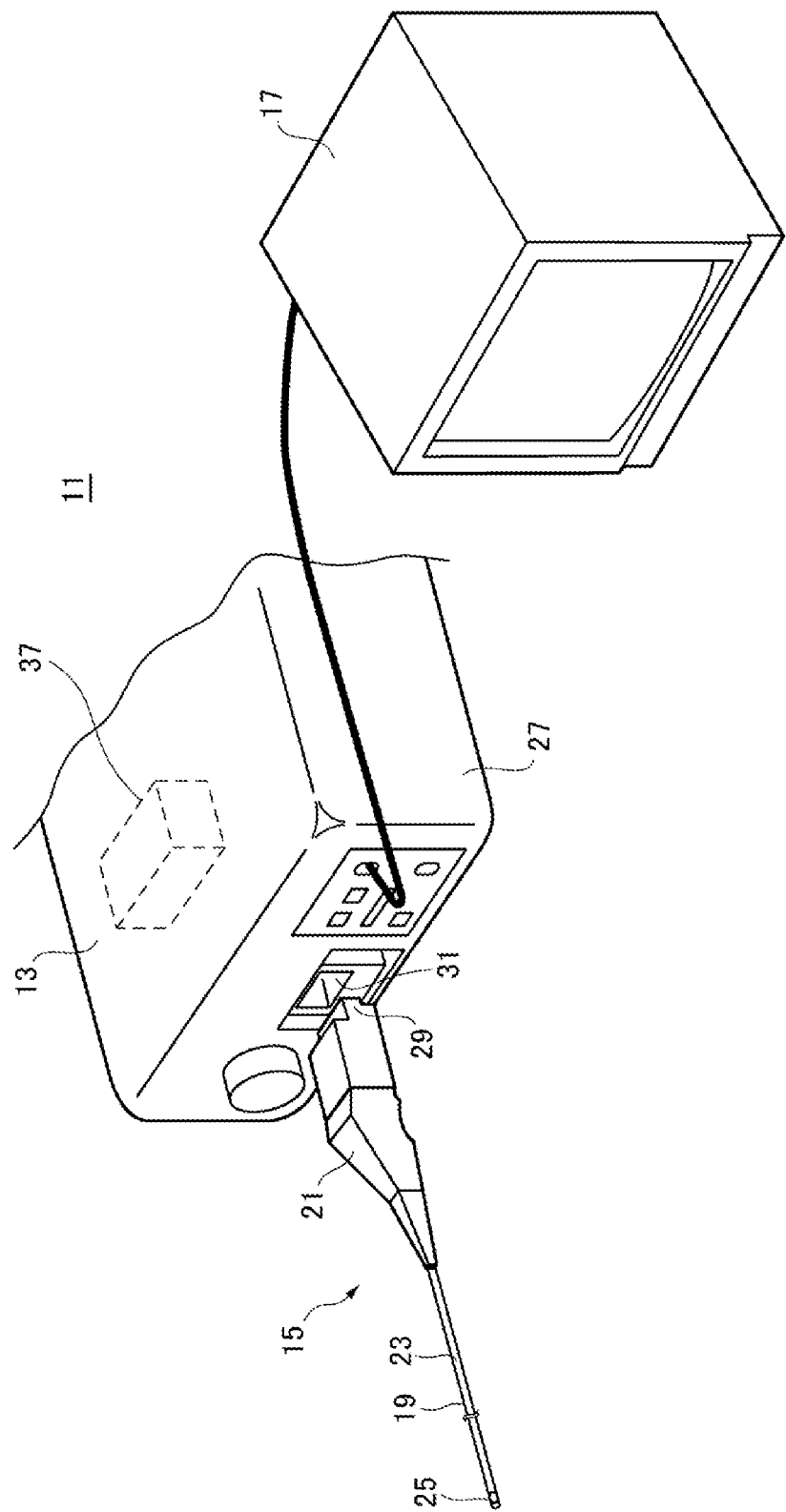
FIG. 1 is a perspective view showing an appearance example of an endoscope system according to a first embodiment.

FIG. 1 is a perspective view showing an appearance example of an endoscope system 11 according to a first embodiment. As terms used herein, an upper direction and a lower direction of a housing 27 of a video processor 13 placed on a horizontal plane are referred to as "upper" and "lower", respectively. Sides where the endoscope 15 captures an observation object are referred to as "front" or "distal", and a side connected to the video processor 13 is referred to as "rear".

The endoscope system 11 includes the endoscope 15, the video processor 13, and a monitor 17. The endoscope 15 is, for example, a hard scope or a flexible scope for medical use as an example of medical equipment. The video processor 13 performs image processing on a captured image (including, for example, a still image and a moving image) obtained by captures the observation object (for example, an affected part of a human body or inside a human body) as a subject. The monitor 17 displays an image in accordance with a display signal output from the video processor 13. The image processing includes, for example, color correction, tone correction, and gain adjustment, but is not limited to these processes.

The endoscope 15 captures the observation object. The endoscope 15 includes a scope 19 inserted into the observation object and a plug portion 21 to which a rear end portion of the scope 19 is connected. The scope 19 includes a relatively long flexible portion 23 having flexibility and a hard portion 25 having rigidity provided at a distal end of the flexible portion 23.

The video processor 13 has a housing 27, performs image processing on the captured image, and outputs a display signal after image processing. A socket portion 31 into which a base end portion 29 of the plug portion 21 is inserted is disposed on a front surface of the housing 27. Since the plug portion 21 is inserted into the socket portion 31 and the endoscope 15 and the video processor 13 are conductively connected, power and various signals (for example, a captured image signal or a control signal) can be transmitted and received between the endoscope 15 and the video processor 13. The power and various signals are transmitted from the plug portion 21 to the flexible portion 23 via a transmission cable 33 (see FIG. 2) inserted into the scope 19. The captured image signal output from an image sensor 35 (see FIG. 4) provided inside the hard portion 25 is transmitted from the plug portion 21 to the video processor 13 via the transmission cable 33.

The video processor 13 performs image processing on the captured image signal transmitted via the transmission cable 33, converts the image data after image processing into a display signal, and outputs it to the monitor 17.

The monitor 17 includes a display device such as a liquid crystal display (LCD), a cathode ray tube (CRT), or the like. The monitor 17 displays a captured image of the subject captured by the endoscope 15. The monitor 17 displays a visible light image captured by illumination of visible light (namely, white light) for illuminating the observation object, and a fluorescence image in which fluorescence generated by excitation light for causing the observation object to emit fluorescence is captured.

An Infrared Ray (IR) excitation light source 37, which is a light source of IR excitation light as an example of excitation light, is provided in the housing 27 of the video processor 13. A light guide body, which is an illumination means, is inserted into the endoscope 15. In the endoscope 15, since the plug portion 21 is inserted into the socket portion 31, the IR excitation light emitted from the IR excitation light source 37 is transmitted to the light guide body of the endoscope 15.

Figure 2:
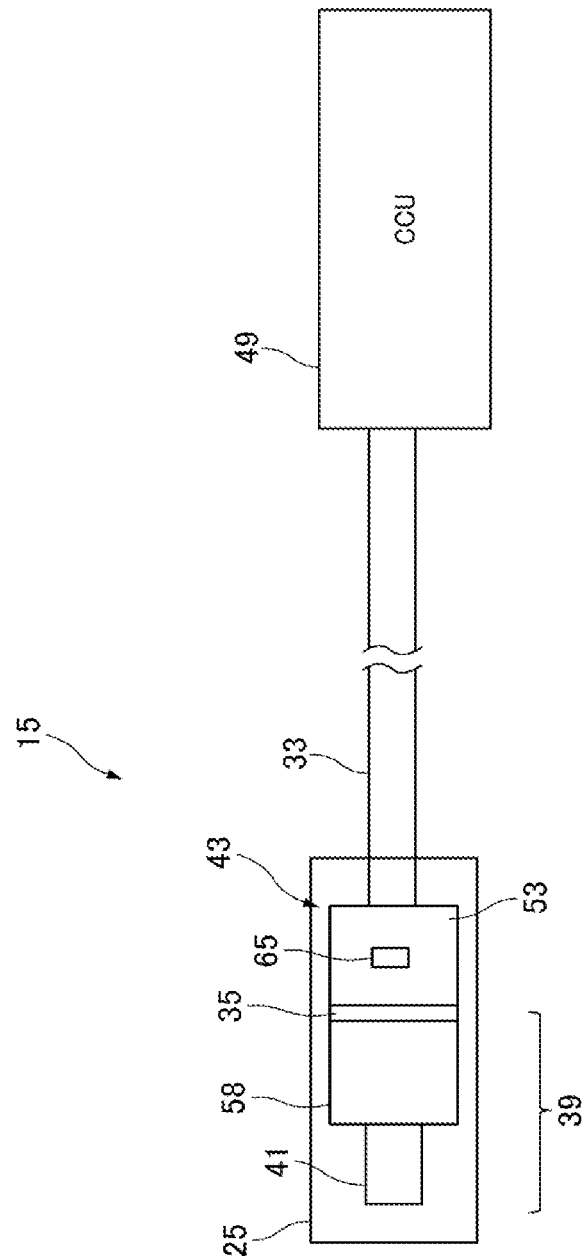
FIG. 2 is a schematic diagram showing a schematic configuration of the endoscope system shown in FIG. 1.

FIG. 2 is a schematic diagram showing a schematic configuration of the endoscope system 11 shown in FIG. 1. A camera 39 (see FIG. 4) as an example of an image capturing portion is provided in the hard portion 25. The camera 39 is integrally provided with a lens unit 41 on a distal end side and an image sensor 35 on a rear end side. The image sensor 35 is conductively connected to a flexible substrate 43 which is a substrate. The transmission cable 33 is conductively connected to the flexible substrate 43. That is, the camera 39 housed in the hard portion 25 is conductively connected to the distal end of the transmission cable 33 drawn into the hard portion 25 via the flexible substrate 43. A voltage conversion device (to be described later) is mounted on the flexible substrate 43.

Figure 3:
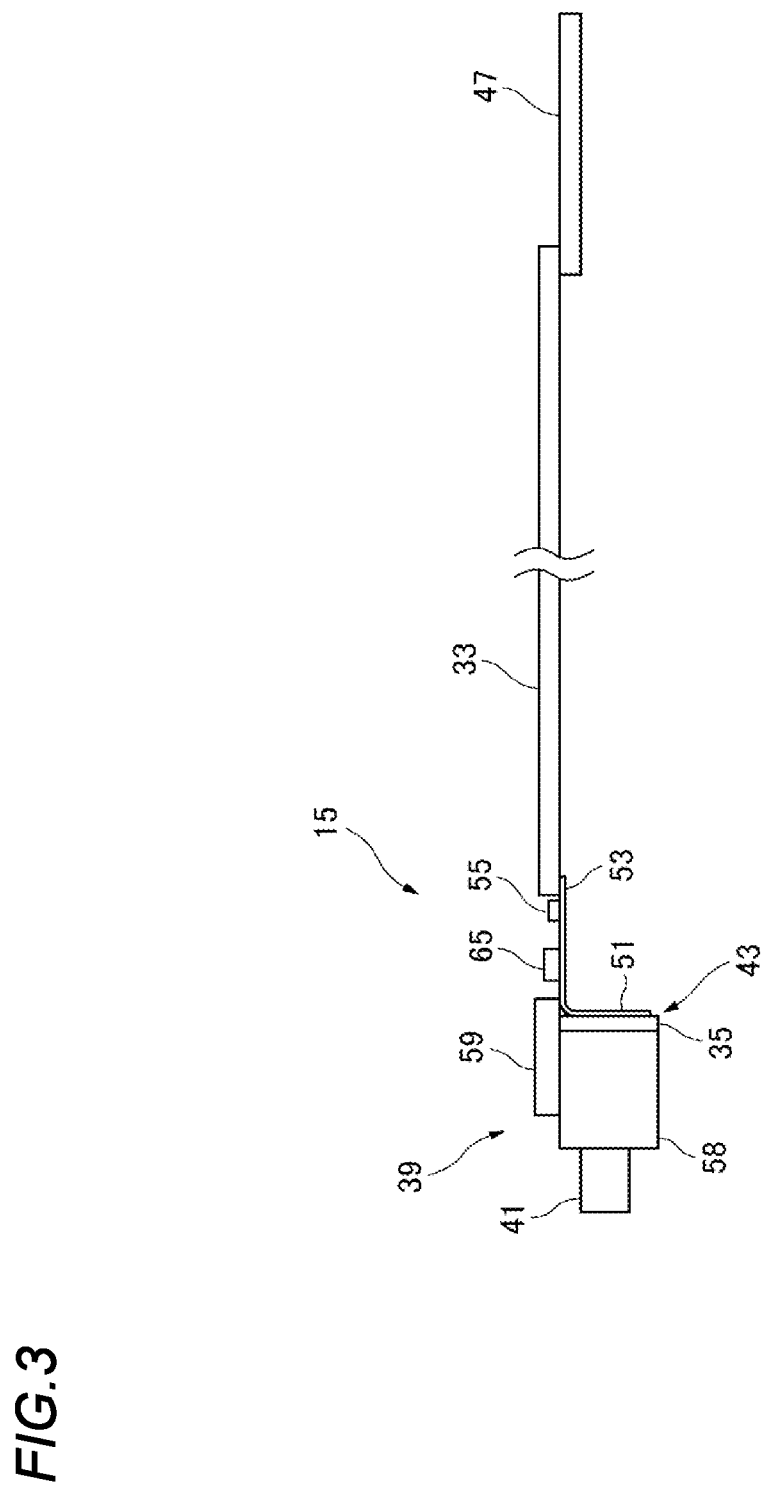
FIG. 3 is a side view showing a configuration of a main part by rotating the endoscope shown in FIG. 2 by 90 degrees around an axis.

FIG. 3 is a side view showing a configuration of a main part by rotating the endoscope 15 shown in FIG. 2 by 90 degrees around an axis. A plurality of pads are provided on a back surface of the image sensor 35. The flexible substrate 43 is conductively connected to the back surface of the image sensor 35 via the pads. The flexible substrate 43 is disposed between the image sensor 35 and the transmission cable 33 to relay both. On the flexible substrate 43, for example, a circuit pattern in which a plurality of linear conductors are pattern printed is formed. The flexible substrate 43 conductively connects each electric wire 45 (see FIG. 4) provided in the transmission cable 33 to the circuit pattern. Thus, the image sensor 35 is connected to the transmission cable 33 via the flexible substrate 43. A base end of the transmission cable 33 is conductively connected to a CCU 49 (see FIG. 2) of a transmission source substrate 47 (see FIG. 3) housed in the video processor 13 via the plug portion 21.

The flexible substrate 43 is formed by bending into an L shape with a sensor connection portion 51 parallel to the back surface of the image sensor 35 and a cable connection portion 53 perpendicular to the back surface. In the flexible substrate 43, a front surface of the sensor connection portion 51 is conductively connected to a pad provided on the back surface of the image sensor 35. On the other hand, a plurality of terminal portions exposed on an upper surface of the cable connection portion 53 are conductively connected to respective electric wires 45 of the transmission cable 33. In addition to the electric wires 45, a plurality of lands for mounting the voltage conversion device and the condenser 55 are formed on the upper surface of the cable connection portion 53. In the present embodiment, as an example, two voltage conversion devices for 3.3 V output and 1.2 V output are mounted. The condenser 55 is mounted on the same surface as a mounting surface of the voltage conversion device. A mounting position and the number of the voltage conversion device or the condenser 55 are not limited to the example shown in FIG. 3.

In the present embodiment, in the endoscope 15, the voltage conversion device and the image sensor 35 are mounted on the same flexible substrate 43.

The flexible substrate 43 can be formed in an L shape by bending a planar substrate. Therefore, in the flexible substrate 43, the image sensor 35, the voltage conversion device, and the condenser 55 can be mounted on the same surface side. That is, components are mounted on one side of the flexible substrate 43. Since components are mounted on one side of the flexible substrate 43, it is not only possible to realize cost reduction due to minimization of time (for example, tact time) required for a mounting step during a solder reflow step, and it is possible to reduce drop or the like of the mounted components as compared with both-side mounting.

Sensor cover glass 57 is stuck on a front surface side of the image sensor 35. The sensor cover glass 57 that fixes the image sensor 35 is fixed to a holder 58 serving as a positioning means. The holder 58 fixes a lens unit 41 to a front portion. An optical axis of the image sensor 35 and the lens unit 41 is positioned via the holder 58. An eaves portion 59 is integrally fixed to an upper surface of the holder 58. The eaves portion 59 extends over a front end of the cable connection portion 53. The eaves portion 59 fixes the front end of the cable connection portion 53.

As the flexible substrate 43, a flexible flat cable (FFC) formed in a belt-shaped cable having flexibility, a flexible printed circuit board (FPC) in which a linear conductor is pattern printed on an insulating substrate having flexibility, and the like can be used by covering a conductor formed of a plurality of strip-shaped thin plates with an insulating sheet material.

Figure 4:
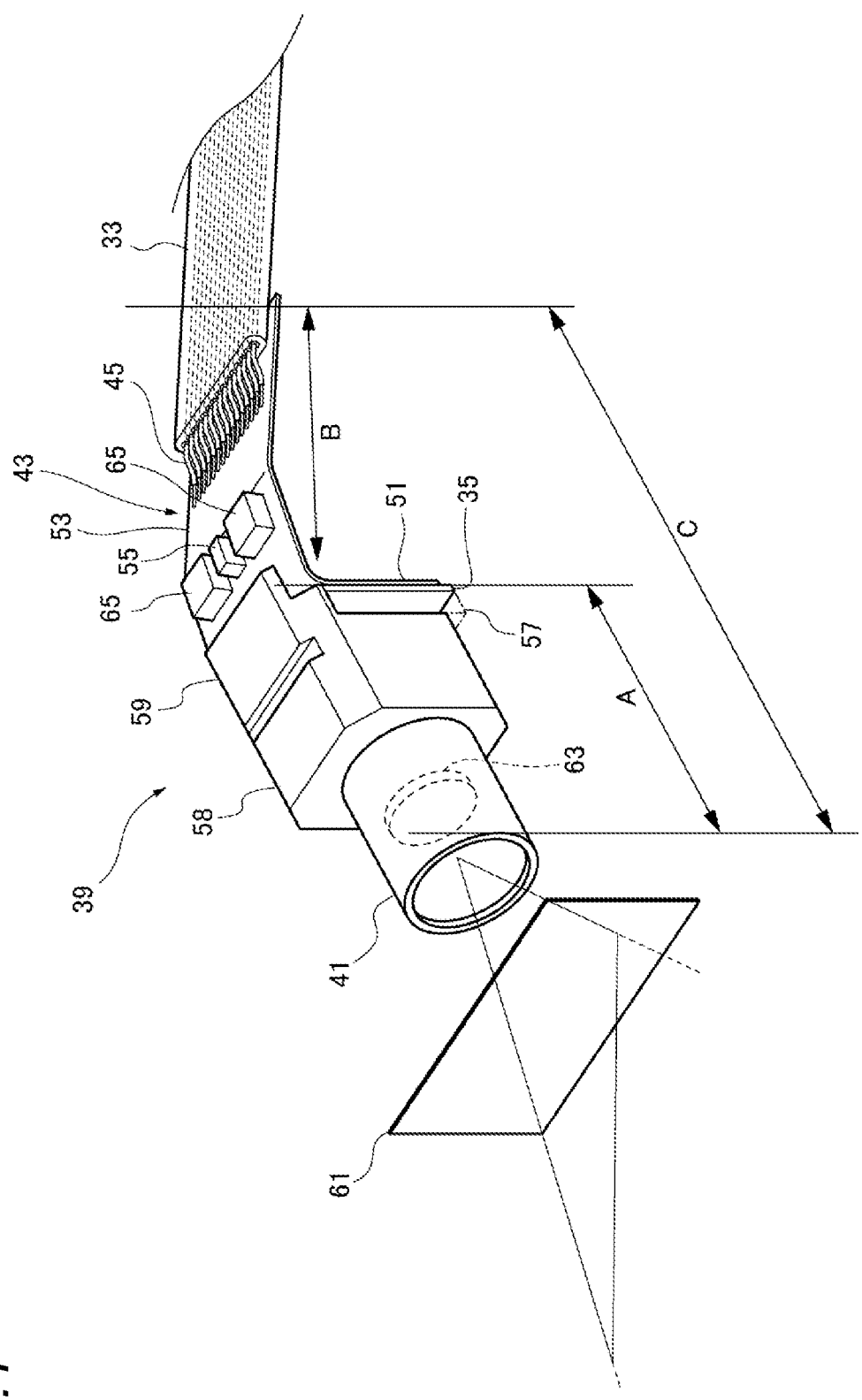
FIG. 4 is a main part enlarged perspective view of the endoscope shown in FIG. 3.

FIG. 4 is a main part enlarged perspective view of the endoscope 15 shown in FIG. 3. In the endoscope 15, the camera 39 and the flexible substrate 43 are housed in the hard portion 25. The camera 39 is formed with a length of A (for example, about 4.6 mm) in a front-rear direction. The flexible substrate 43 is formed with a length of B (for example, about 5.3 mm) in the front-rear direction. The hard portion 25 is formed with a length of C (for example, about 10 mm) in the front-rear direction. Therefore, the camera 39 and the flexible substrate 43 can be housed inside the hard portion 25 (A+B<C). The hard portion 25 can be formed by molding the camera 39 and the flexible substrate 43 with a synthetic resin. The hard portion 25 may house the camera 39 and the flexible substrate 43 in a metallic tube. Further, in the hard portion 25, a bonding material may be filled in the metallic tube that house the camera 39 and the flexible substrate 43. In either case, the hard portion 25 is formed into a cylindrical shape having rigidity. The transmission cable 33 is derived from the rear end of the hard portion 25. The derived transmission cable 33 is covered with a sheath (not shown) made of a soft material provided on an outer diameter of the scope 19.

An image capturing window 61 is disposed on a distal end surface of the hard portion 25. The image capturing window 61 is formed including an optical material such as optical glass and optical plastic, and light from the subject is incident. The lens unit 41 of the camera 39 is disposed behind the image capturing window 61. The lens unit 41 includes lens cover glass which is an optical component, a diaphragm, a plurality of lenses, a spacer 63, and the like inside the lens barrel. The sensor cover glass 57 stuck on the image sensor 35 is positioned on the holder 58 to be disposed behind the lens unit 41.

Figure 5:
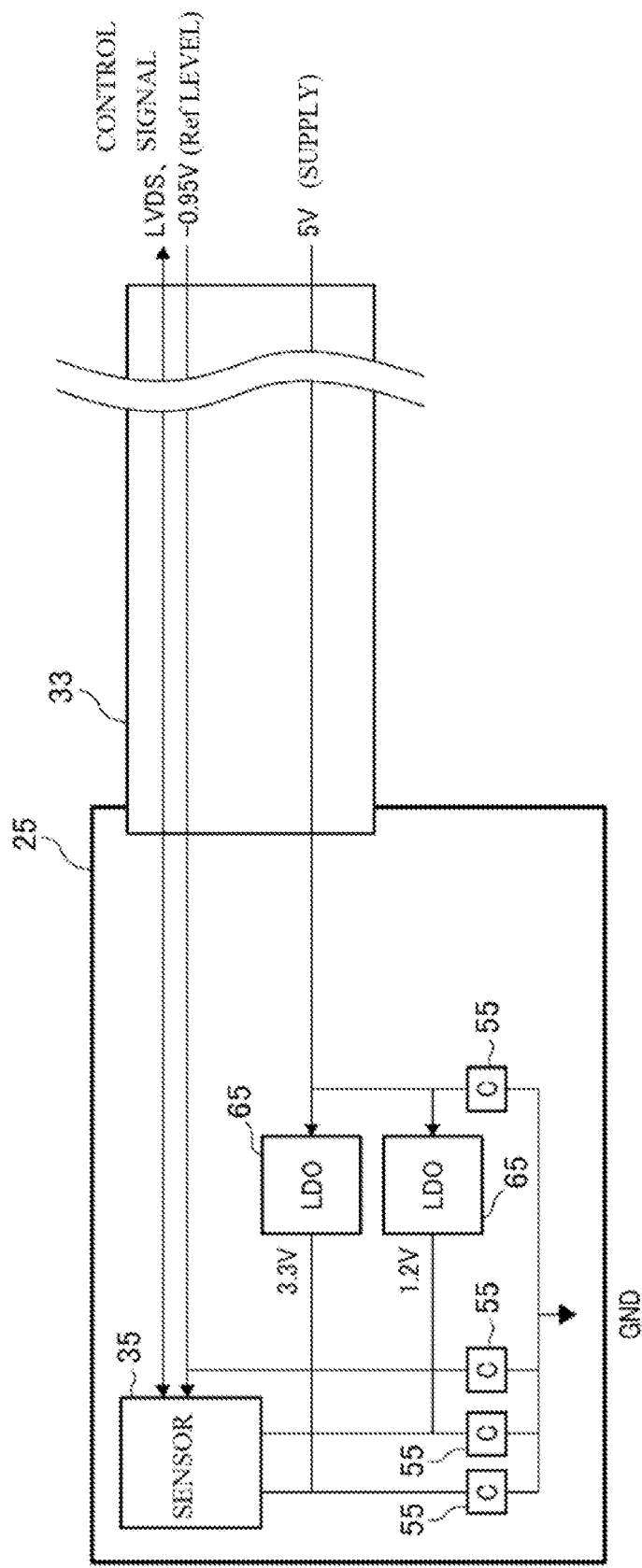
FIG. 5 is a block diagram showing an example of a circuit in a hard portion shown in FIG. 4.

FIG. 5 is a block diagram showing an example of a circuit in a hard portion 25 shown in FIG. 4. The voltage conversion device mounted on the cable connection portion 53 of the flexible substrate 43 can output a constant voltage from an output terminal to the image sensor 35 with respect to an input voltage input (in other words, supplied or applied) from the transmission cable 33 to an input terminal. In the present embodiment, as described above, two voltage conversion devices for 3.3 V output and 1.2 V output are mounted.

In the present embodiment, the voltage conversion device is a linear regulator.

Further, the linear regulator is an LDO regulator 65.

An electric supply source (for example, 5 V) and the condenser 55 on an input side are connected between respective input terminals of a pair of LDO regulators 65, 65 and the ground (GND). A plurality of condensers 55 on output sides are connected between respective output terminals of the pair of LDO regulators 65, 65 and the GND. Accordingly, even though 5V is supplied from the electric supply source and a voltage droop occurs due to resistance depending on a length of the transmission cable 33, one LDO regulator 65 in the pair of LDO regulators 65 capable of corresponding to a wide range of input voltage can stably output a constant voltage (3.3 V) from the output terminal to the image sensor 35. In the same way, the other LDO regulator 65 can stably output a constant voltage (1.2 V) from the output terminal to the image sensor 35. In the endoscope 15, these circuits (see FIG. 5) have a basic circuit configuration.

The image sensor 35 transmits a serial image capturing signal to the transmission cable 33 by a differential method (for example, a low voltage differential signaling (LVDS) method). In the present embodiment, although a reference level (Ref level) for causing the image sensor 35 to function as a comparator is −0.95 V, but when an image sensor of a type not having the function as a comparator is used, supply of the reference level (for example, −0.95 V) may be omitted.

With the circuit configuration, in the endoscope 15, even though a voltage droop occurs, as long as the voltage is within an input voltage range capable of corresponding to the LDO regulator 65, a constant voltage (3.3 V, 1.2 V) can be stably output even for the voltage droop by increasing the supply voltage to a limit of 5 V during extension of the transmission cable 33.

Next, the operation of the endoscope 15 according to the present embodiment will be described.

The endoscope 15 according to the present embodiment includes the scope 19 provided with the hard portion 25 at the distal end of the long flexible portion 23 having flexibility, an image capturing portion (for example, camera 39) having the image sensor 35 housed in the hard portion 25, and the transmission cable 33 inserted into the scope 19 and conductively connected to the image sensor 35 at a distal end via the flexible substrate 43. The endoscope 15 includes a voltage conversion device mounted on the flexible substrate 43 and outputting a constant voltage to the image sensor 35 with respect to the input voltage input to the transmission cable 33. That is, the voltage conversion device is mounted on the flexible substrate 43 that relaying connects the distal end of the transmission cable 33 and the image sensor 35. The voltage conversion device always outputs a constant voltage to the image sensor 35 with respect to the input voltage input to the transmission cable 33.

In recent years, there is an increasing demand for improving resolution even in the endoscope 15. When the image sensor 35 is also in a high definition (HD) class or more, not only the LVDS is used for a signal line, a large number of control lines including a plurality of power supply lines for the image sensor are also necessary. For this reason, in the endoscope 15, it is necessary to pass ten-odd to 20 electric wires 45 through the small diameter scope 19.

Each electric wire 45 of the transmission cable 33 is required to have a small diameter of less than wire No. AWG42 (a cross-sectional diameter or a maximum parallel facing distance is about 0.08 mm) in order to ensure a minimum limit of current. Further, since the transmission cable 33 needs to extend several meters or more (for example, 3 to 4 m) to a controller, a voltage droop is caused due to a considerably large internal resistance value.

Here, the voltage droop includes additional problems. That is, in an electrical circuit such as the image sensor 35, since impedance of the internal circuit is different between the time of operation and the time of non-operation such as the time of Sleep, a droop level of the voltage droop varies.

Therefore, in the endoscope 15, the problems are solved by mounting the voltage conversion device (for example, the LDO regulator 65) on a substrate connected to the distal end of the transmission cable 33. The voltage conversion device can obtain a constant voltage by a single device. Therefore, it is not necessary to house an adjustment circuit including the condenser 55, a resistor, a coil, and the like in the distal end (hard portion 25) of the scope 19. As a result, an increase in diameter of the distal end portion (for example, the hard portion 25) can be reduced in the endoscope 15. In other words, space that can be effectively used can be ensured as the condenser 55, the resistor, the coil, and the like are not required as compared with a configuration provided with the adjustment circuit.

Since the voltage conversion device operates even with a large voltage difference between input and output, it is possible to input a constant voltage to the image sensor 35 in the hard portion 25 regardless of operation or non-operation of the image sensor 35. Accordingly, the operation of the image sensor 35 can be stabilized.

In this way, in the endoscope 15 in which the voltage conversion device is mounted at the distal end, since the voltage droop can be reduced even in the electric wire 45 that has a small diameter and reaches 3 to 4 m, it is possible to stably realize high resolution of an observed image while reducing an increase in diameter of the scope 19. Therefore, according to the endoscope 15 according to the present embodiment, even though the transmission cable 33 of the video signal obtained from the image capturing portion (for example, camera 39) disposed in the distal end portion (for example, hard portion 25) is long, it is possible to obtain a high-resolution video signal by stably operating the image capturing portion (for example, camera 39) at high resolution while reducing an increase in diameter of the distal end portion (for example, hard portion 25).

In the endoscope 15, the voltage conversion device is a linear regulator.

In addition, in the endoscope 15, the voltage conversion device can be simplified. That is, in the LDO regulator 65, for example, a switching lens unit or a three-terminal regulator can be used. In the LDO regulator 65, a stable constant voltage can be output from the output terminal only by connecting the condenser 55 on the input side to the power supply between the input terminals and the GND and the condensers 55 on the output sides between the output terminals and the GND. That is, the endoscope 15 can realize a configuration in which a stable constant voltage can be output from the output terminal in limited space.

In the endoscope 15, the voltage conversion device is the LDO regulator 65.

In addition, in the endoscope 15, the voltage conversion device may be a low dropout regulator (LDO) regulator 65. The LDO regulator 65 has a high input voltage, a low dropout voltage, and operates at low power. That is, the LDO regulator 65 operates in a large voltage difference between input and output. The LDO regulator 65 can supply a high-precision constant voltage to the image sensor 35. Accordingly, image capturing precision of the image sensor 35 can be improved. Further, since it is easy to miniaturize a package of the LDO regulator 65, it is suitable for reducing the diameter of the endoscope 15.

In the endoscope 15, the voltage conversion device and the image sensor 35 are mounted on the same substrate.

In the endoscope 15, the LDO regulator 65 and the image sensor 35 are mounted on the same flexible substrate 43. In the present embodiment, the LDO regulator 65 and the image sensor 35 are mounted on the same surface of the flexible substrate 43. Accordingly, the LDO regulator 65 and the image sensor 35 can be placed on an upper surface of the flexible substrate 43 which is flat in a step before bending into an L shape, and a reflow step can be performed at the same time. As a result, it is difficult to detach the mounting component from the flexible substrate 43, and the component mounting that is easy with high reliability can be performed. On the same surface, the flexible substrate 43 on which the LDO regulator 65 and the image sensor 35 are mounted is bent at an approximately right angle at a boundary portion between the LDO regulator 65 and the image sensor 35, and the bent portion is fixed to the eaves portion 59.

Next, modifications of the configuration according to the first embodiment described above will be described.

[First Modification]

Figure 6:
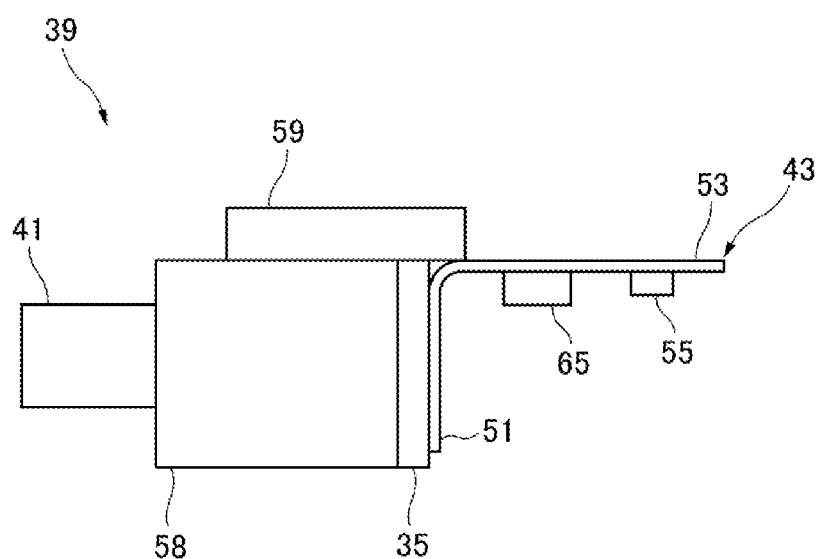
FIG. 6 is a side view showing a configuration of a main part according to a first modification in which components are mounted on both sides of a substrate.

FIG. 6 is a side view showing a configuration of a main part according to a first modification in which components are mounted on both sides of a substrate. An endoscope according to the first modification of the first embodiment has approximately the same configuration as that of the endoscope 15 according to the first embodiment, in which the same component is denoted by the same reference numeral, and description thereof will be simplified or omitted; different contents will be described.

In the endoscope 15 according to the first modification, components are mounted on both sides of the flexible substrate 43. In the first modification, the image sensor 35 is mounted on one side of the flexible substrate 43, and the voltage conversion device or the condenser 55 are mounted on the other side of the flexible substrate 43. That is, in the flexible substrate 43, the LDO regulator 65 and the condenser 55 are disposed on a lower surface (internal corner side) of the cable connection portion 53 bent approximately perpendicular to the sensor connection portion 51.

In the endoscope 15, by mounting components on both sides of the flexible substrate 43, it is possible to dispose the mounting component on the internal corner side of the flexible substrate 43 bent into an L shape, and thus protrusion of the mounting components to the outside can be eliminated. Thus, according to the endoscope 15, since it is possible to contribute to reduction in diameter of the hard portion 25, space for disposing an illumination means such as an optical fiber on an upper side of the flexible substrate 43 can be ensured.

[Second Modification]

Figure 7:
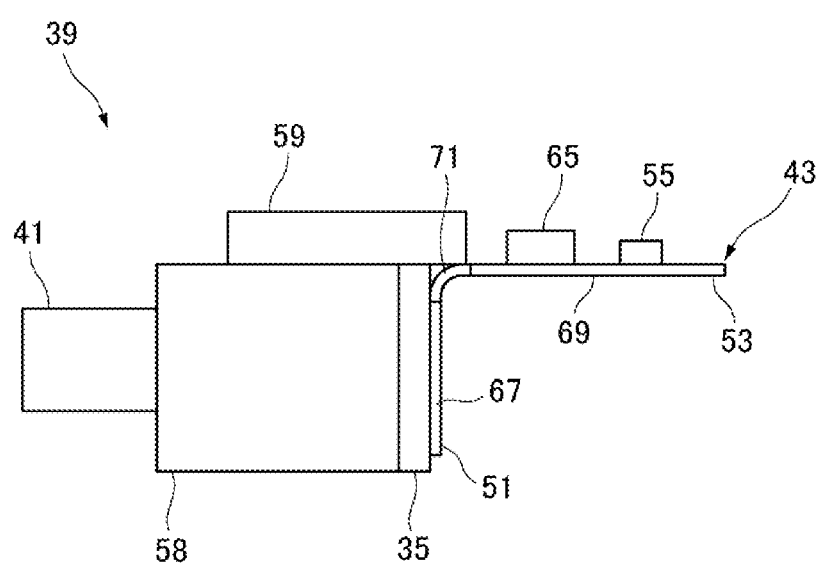
FIG. 7 is a side view showing a configuration of a main part according to a second modification in which a substrate is made of a flexible substrate including a rigid substrate.

FIG. 7 is a side view showing a configuration of a main part according to a second modification in which a substrate is made of the flexible substrate 43 including a rigid substrate. An endoscope according to the second modification of the first embodiment has approximately the same configuration as that of the endoscope 15 according to the first embodiment, in which the same component is denoted by the same reference numeral, and description thereof will be simplified or omitted; different contents will be described.

In the endoscope 15 according to the second modification, the substrate (for example, the flexible substrate 43) includes a first rigid substrate 67 and a second rigid substrate 69 connected by a thin hinge portion 71 having flexibility. In the flexible substrate 43, the image sensor 35 is mounted on the first rigid substrate 67, and the voltage conversion device is mounted on the second rigid substrate 69. The image sensor 35 and the voltage conversion device are mounted on the same surface of the first rigid substrate 67 and the second rigid substrate 69 in a flatly developed state.

The first rigid substrate 67 and the second rigid substrate 69 are connected by the thin hinge portion 71 to form a substrate having an integrated composite structure (for example, the flexible substrate 43). The flexible substrate 43 having the composite structure covers, for example, a sensor mounting pattern portion connected to the image sensor 35 and a device mounting pattern portion integrally formed with the sensor mounting pattern portion and connected to the voltage conversion device with a hard insulating resin. At this time, a non-covered portion that is not covered by a hard insulating resin is left at a boundary portion between the sensor mounting pattern portion and the device mounting pattern portion. The non-covered portion is covered with, for example, a soft insulating resin. In the substrate having a composite structure, a part covered with the soft insulating resin can be used as the thin hinge portion 71. Thus, in the flexible substrate 43 having the composite structure, the first rigid substrate 67 and the second rigid substrate 69 can be easily bent via the thin hinge portion 71. The thin hinge portion 71 has the same thickness as the first rigid substrate 67 and the second rigid substrate 69, and is formed of, for example, a member made of a thin material having flexibility. A method of producing the substrate according to the second modification is not limited thereto.

In the endoscope 15, the substrate includes a first rigid substrate 67 and a second rigid substrate 69 connected by a hinge portion (for example, the thin hinge portion 71) having flexibility. The image sensor 35 is mounted on the first rigid substrate 67, and the voltage conversion device is mounted on the second rigid substrate 69.

In the endoscope 15, the substrate (for example, the flexible substrate 43) includes the first rigid substrate 67 and the second rigid substrate 69 which are hard, and the thin hinge portion 71 having flexibility which is soft and connects them. In the substrate having the composite structure, the first rigid substrate 67 and the second rigid substrate 69 having high rigidity on which the image sensor 35 and the voltage conversion device are mounted can be easily bent by the thin hinge portion 71 having flexibility. Accordingly, the substrate can be deformed into any bent shape adapted to limited internal space of the hard portion 25. As a result, assembling properties of the image capturing portion to the hard portion 25 can be improved.

[Third Modification]

Figure 8:
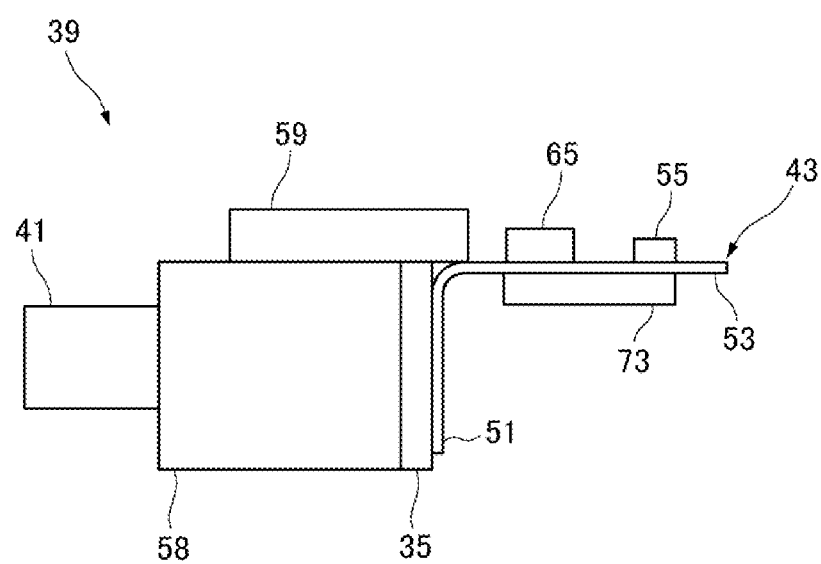
FIG. 8 is a side view showing a configuration of a main part according to a third modification in which a wireless device is mounted on a substrate.

FIG. 8 is a side view showing a configuration of a main part according to a third modification in which a wireless device 73 is mounted on a substrate. An endoscope according to the third modification of the first embodiment has approximately the same configuration as that of the endoscope 15 according to the first embodiment, in which the same component is denoted by the same reference numeral, and description thereof will be simplified or omitted; different contents will be described.

In the endoscope 15 according to the third modification, the wireless device 73 is mounted on the flexible substrate 43. The wireless device 73 is mounted on a lower surface of the cable connection portion 53 on which the voltage conversion device or the condenser 55 is mounted. As described above, in the endoscope 15, as compared with the configuration provided with the adjustment circuit, it is possible to secure space that can be effectively used on the substrate. The wireless device 73 is loaded by using the space.

Figure 9:
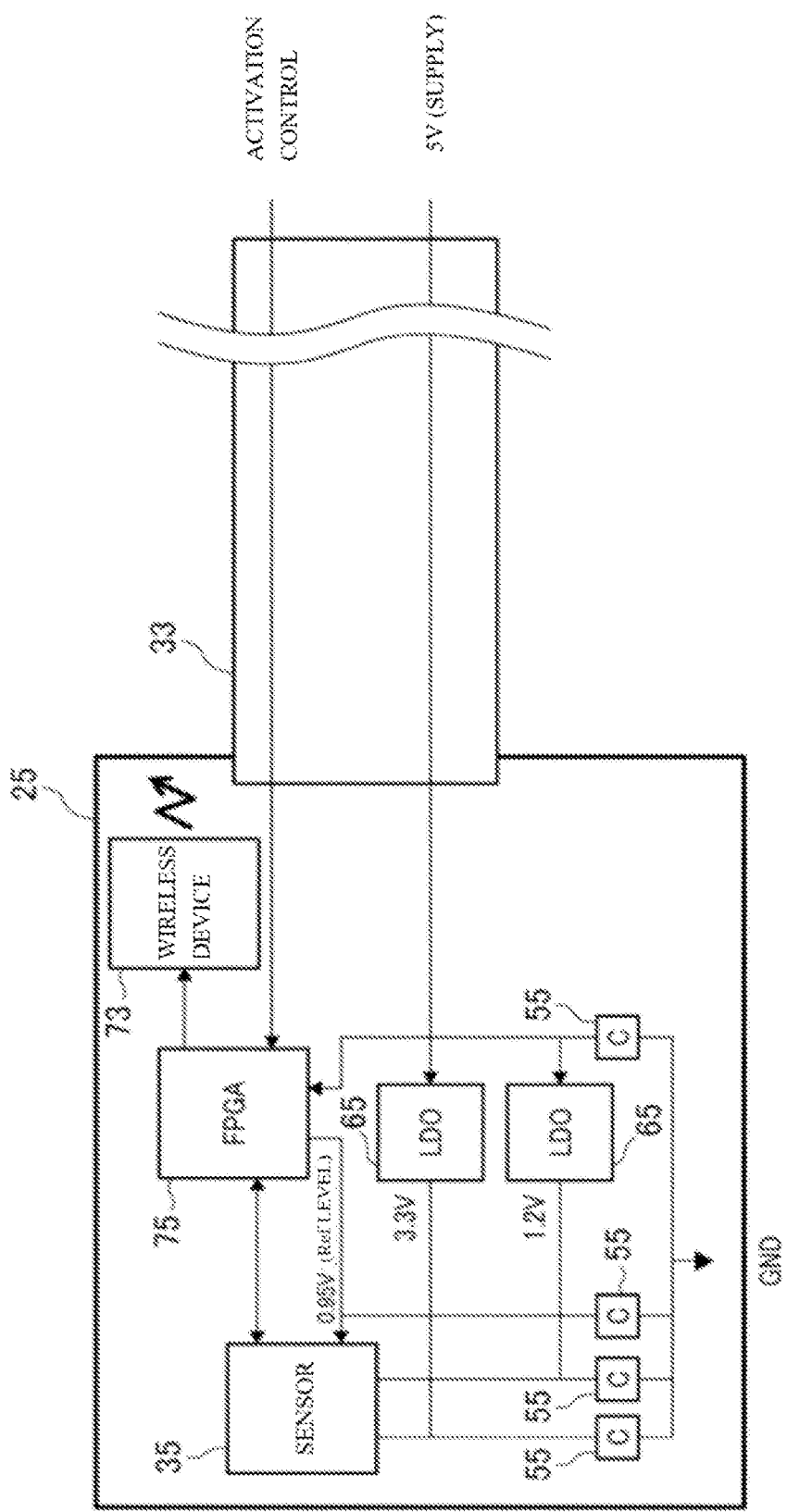
FIG. 9 is a block diagram showing an example of a circuit in a hard portion according to a third modification.

FIG. 9 is a block diagram showing an example of a circuit in the hard portion 25 according to the third modification. The endoscope 15 according to the third modification includes the wireless device 73, and thus transmission and reception of a control signal having the basic circuit configuration shown in FIG. 5 are performed by the wireless device 73. That is, wirelessness is possible by using space such as a back surface of the cable connection portion 53. Therefore, a control signal line can be not required. The wireless device 73 wirelessly transmits and receives the control signal to and from a transmission and reception portion provided on the transmission source substrate 47.

In addition to the basic circuit configuration shown in FIG. 5, a field programmable gate array (FPGA) 75 or the like connected to the wireless device 73 is provided on the flexible substrate 43. The FPGA 75 is a programmable logic device capable of rewriting processing contents. The image sensor 35 is controlled by using a control signal (for example, the reference signal described above) generated by the FPGA 75 based on the control signal from the transmission source substrate 47 input from the wireless device 73. In the endoscope 15 according to the third modification, stabilization due to an interface of the image sensor 35 and generation of Ref voltage is possible by mounting the FPGA 75.

In the endoscope 15, the wireless device 73 is mounted on the substrate.

In the endoscope 15, by providing the voltage conversion device, the space secured on the substrate can be effectively used to provide the wireless device 73 and the FPGA 75. By mounting of the FPGA 75 and wirelessness, the control signal to the image sensor 35 can be limited to an activation signal. Accordingly, the control signal line necessary in the basic circuit configuration can be not required. As a result, it is possible to reduce the number of wires of the transmission cable 33 and to contribute to reduction in diameter of the endoscope 15.

[Fourth Modification]

Figure 10:
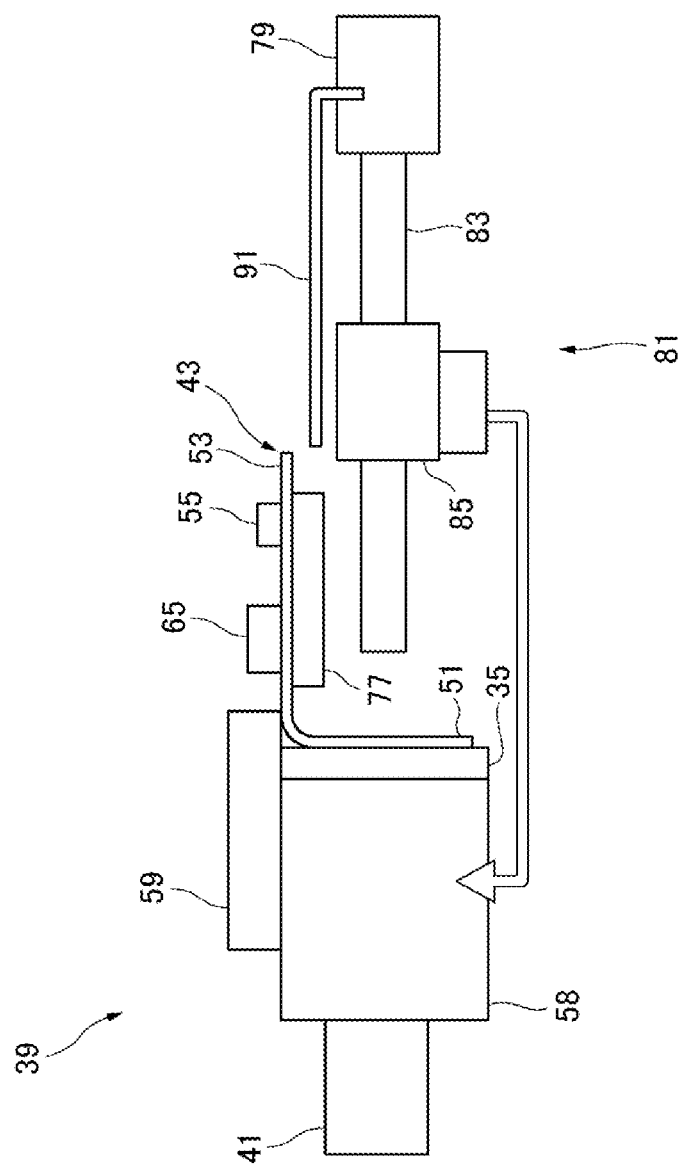
FIG. 10 is a side view showing a configuration of a main part according to a fourth modification in which a driving device is mounted on a substrate.

FIG. 10 is a side view showing a configuration of a main part according to a fourth modification in which a driving device is mounted on a substrate. An endoscope according to the fourth modification of the first embodiment has approximately the same configuration as that of the endoscope 15 according to the first embodiment, in which the same component is denoted by the same reference numeral, and description thereof will be simplified or omitted; different contents will be described.

In the endoscope 15 according to the fourth modification, a motor driving device 77 is mounted on the flexible substrate 43. The hard portion 25 is provided with a motor 79 and a lens system driving mechanism 81 such as an autofocus driven by the motor 79. The lens system driving mechanism 81 includes a screw shaft 83 driven by the motor 79, a nut portion 85 screwed to a screw shaft 83, and a movable lens bracket 89 (see FIG. 12) that is fixed to the nut portion 85 and supports a movable lens group 87.

Figure 11:
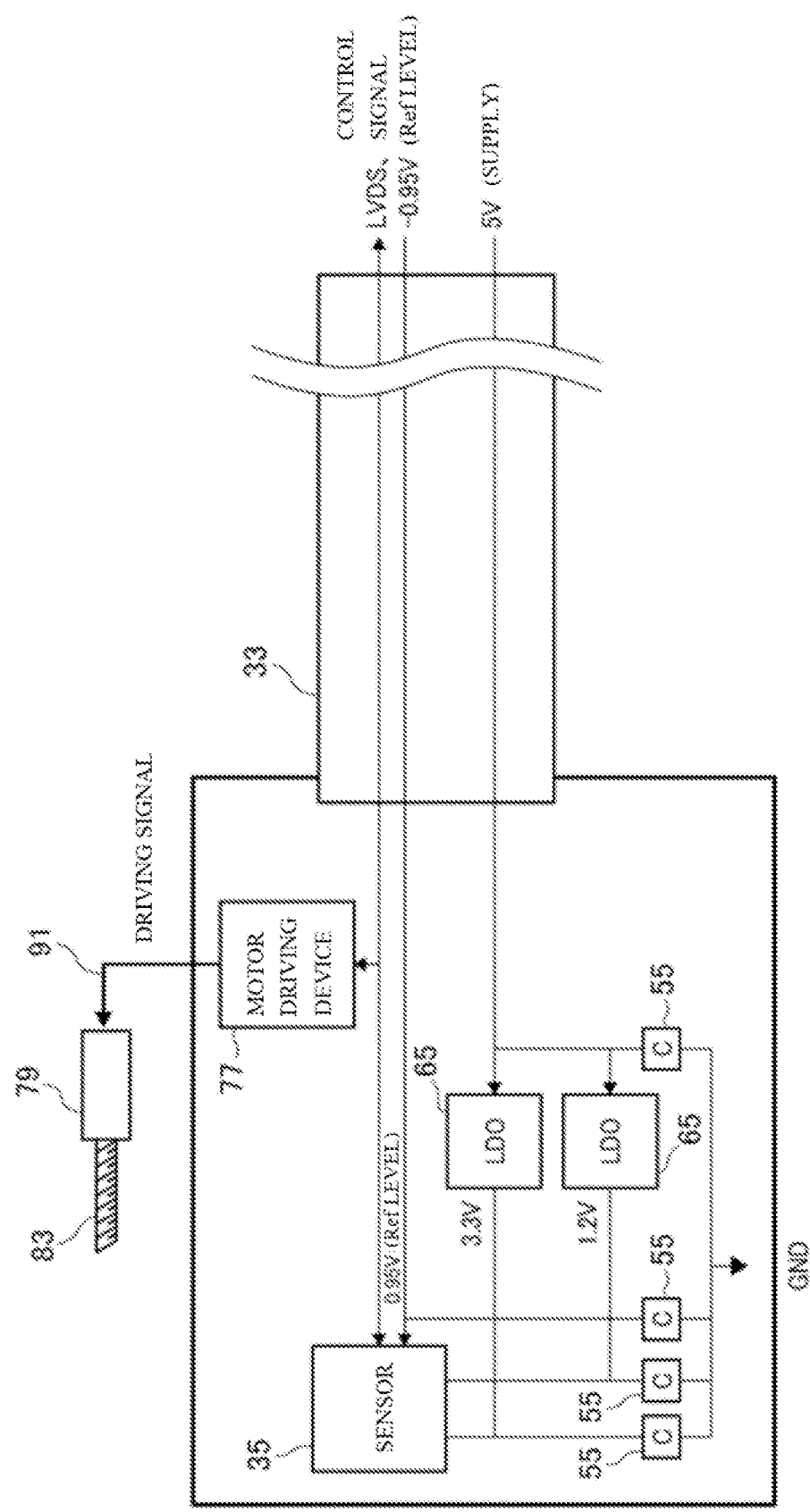
FIG. 11 is a block diagram showing an example of a circuit in a hard portion according to the fourth modification.

FIG. 11 is a block diagram showing an example of a circuit in the hard portion 25 according to the fourth modification. The endoscope 15 according to the fourth modification includes the motor driving device 77, and thus the motor driving device 77 is connected to the control signal line having the basic circuit configuration shown in FIG. 5. That is, autofocus is possible by using space such as the back surface of the cable connection portion 53. In the motor driving device 77, control is possible by an I/F driving device of communication control (I2C and the like) in the control signal. A power supply for driving the motor driving device 77 can share a power supply on an output side of the supply source power supply or the LDO regulator 65.

Figure 12:
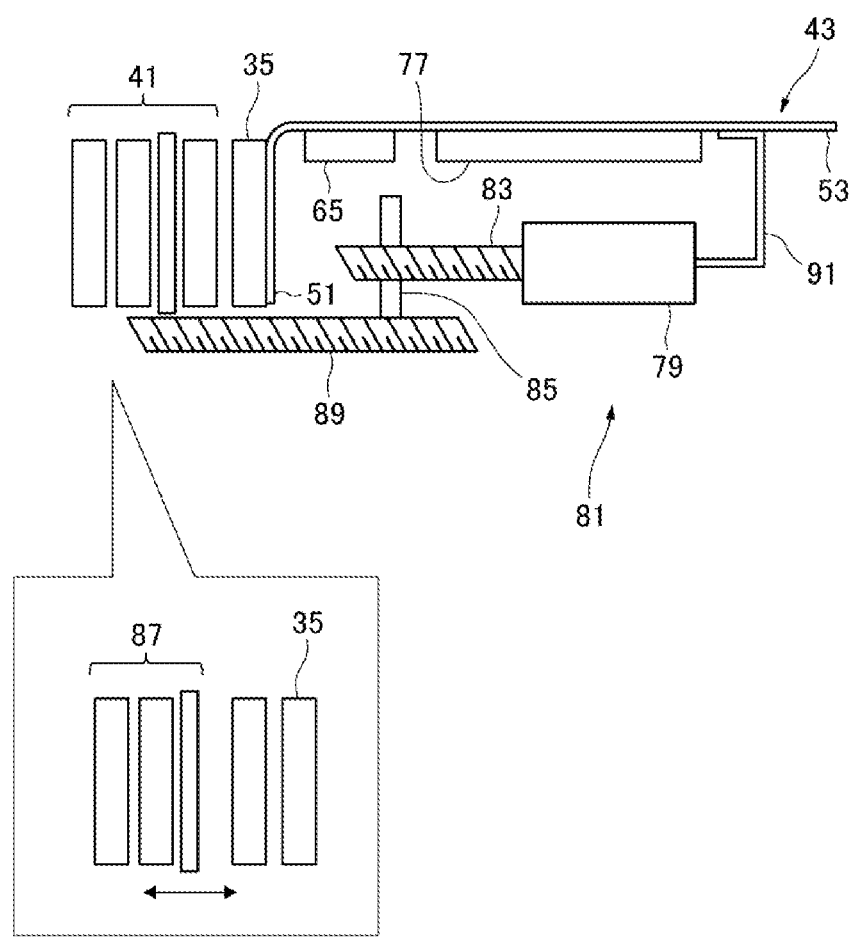
FIG. 12 is a main part explanatory diagram illustrating a lens system driving mechanism according to the fourth modification together with a lens operation diagram.

FIG. 12 is a main part explanatory diagram illustrating the lens system driving mechanism 81 according to the fourth modification together with a lens operation diagram. In the endoscope 15, when a control signal from the motor driving device 77 is sent to the motor 79 via a motor harness 91, the motor 79 is controlled to rotate at a predetermined rotation angle in forward and backward directions. When the screw shaft 83 is rotated at the predetermined rotation angle, the movable lens group 87 is moved with respect to the image sensor 35 by the movable lens bracket 89 supported by the nut portion 85 to focus on the subject. An operation amount for positioning the movable lens group 87 by the motor driving device 77 is calculated based on focal length information input from the transmission source substrate 47.

In addition, in the endoscope 15, the motor driving device 77 is mounted on the substrate.

In the endoscope 15, by providing the voltage conversion device, the space secured on the substrate can be effectively used to provide the motor driving device 77. The autofocus function can be loaded by the motor driving device 77. As a result, in the endoscope 15, a higher-resolution observation image is obtained, in which the lens unit 41 is focused on the subject with high precision without increasing the diameter of the hard portion 25.

[Fifth Modification]

Figure 13:
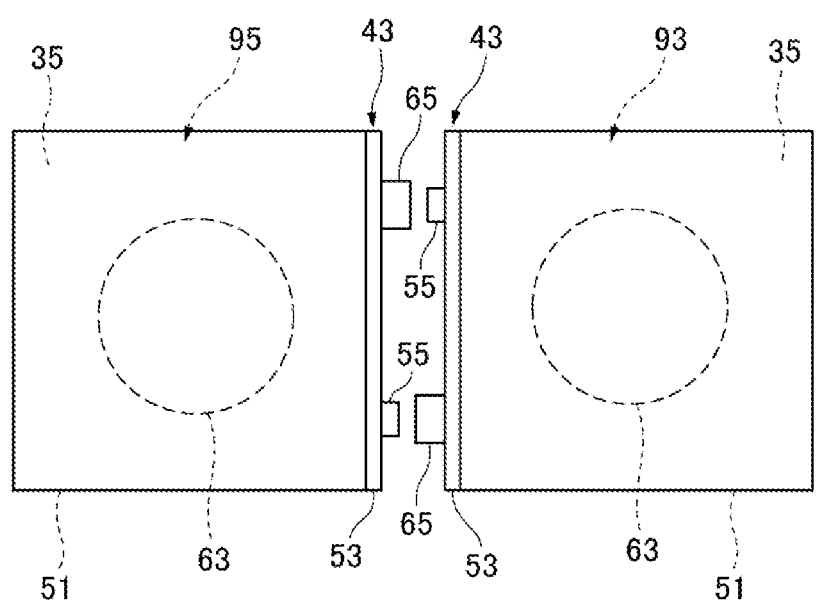
FIG. 13 is a rear view showing a configuration example of substrates according to a fifth modification which become a two-lens camera.

FIG. 13 is a rear view showing a configuration example of substrates according to a fifth modification which become a two-lens camera. An endoscope according to the fifth modification of the first embodiment has approximately the same configuration as that of the endoscope 15 according to the first embodiment, in which the same component is denoted by the same reference numeral, and description thereof will be simplified or omitted; different contents will be described.

In the endoscope 15 according to the fifth modification, the hard portion 25 includes a pair of a right lens camera 93 and a left lens camera 95 with an axis sandwiched therebetween. Each of the substrates connected to each of the image sensors 35 of the right lens camera 93 and the left lens camera 95 is formed by bending into an L shape with the sensor connection portion 51 parallel to the back surface of the image sensor 35 and the cable connection portion 53 perpendicular to the back surface. Here, the cable connection portion 53 is a protruded portion jutted out more outward than an outer shape of the image sensor 35. The right lens camera 93 and the left lens camera 95 are disposed in a direction in which each of the image sensors 35 causes each of the cable connection portions to face each other with the axis of the hard portion 25 sandwiched therebetween. That is, each of the cable connection portions 53 faces inside.

In the endoscope 15, the camera 39 is a two-lens camera including the right lens camera 93 and the left lens camera 95. In the two-lens camera, each of a pair of images captured by each of a pair of linked cameras 39 in which parallax is formed is processed, and a stereoscopic image in which depth information is reflected can be generated and displayed on the monitor 17. The right lens camera 93 and the left lens camera 95 can be the camera 39 having the same specification.

The hard portion 25 of the endoscope 15 includes a pair of image capturing portions with the axis sandwiched therebetween, a substrate connected to the image sensor 35 disposed in each of the pair of image capturing portions is formed by bending into an L shape with the sensor connection portion 51 parallel to the back surface of the image sensor 35 and the cable connection portion 53 perpendicular to the back surface, and each of the image sensors 35 is disposed in a direction in which each of the cable connection portions face each other with the axis of the hard portion 25 sandwiched therebetween.

In the endoscope 15, the hard portion 25 is provided with a pair of the right lens camera 93 and the left lens camera 95. In a configuration that enables generation of the stereoscopic image, since the pair of cable connection portions 53 are disposed inside, it is not only possible to secure wide space for loading the other components or assembling the other components, but also possible to reduce the diameter on both sides of the pair of cable connection portions 53 (respective internal corner sides).

[Sixth Modification]

Figure 14:
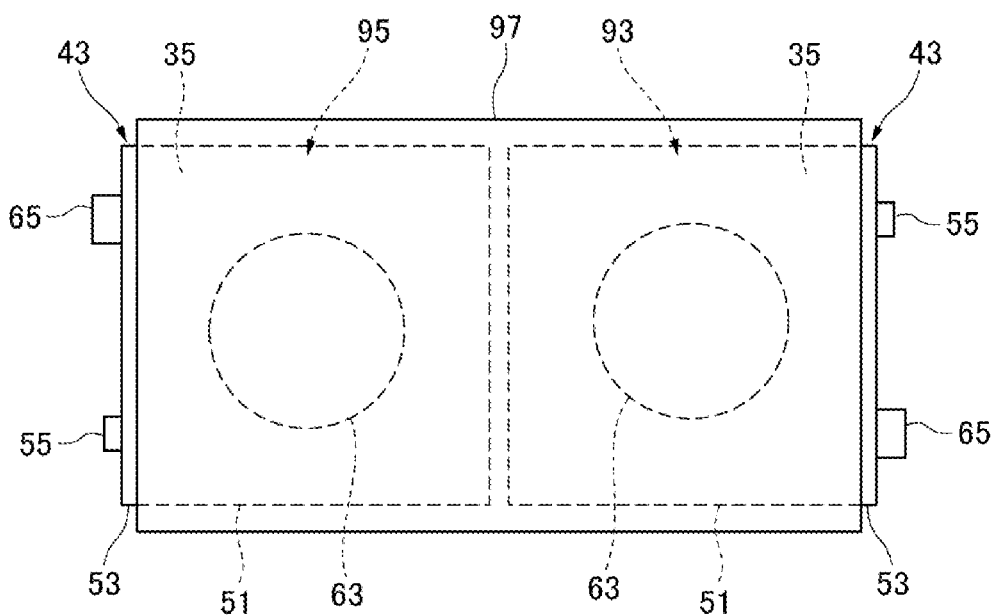
FIG. 14 is a rear view showing a configuration example of shading members according to a sixth modification which become a two-lens camera.

FIG. 14 is a rear view showing a configuration example of shading members 97 according to a sixth modification which become a two-lens camera. An endoscope according to the sixth modification of the first embodiment has approximately the same configuration as that of the endoscope 15 according to the first embodiment, in which the same component is denoted by the same reference numeral, and description thereof will be simplified or omitted; different contents will be described.

As in the fifth modification, the endoscope 15 according to the sixth modification includes a pair of the right lens camera 93 and the left lens camera 95. As in the fifth modification, each of the substrates connected to each of the image sensors 35 of the right lens camera 93 and the left lens camera 95 is formed by bending into an L shape with the sensor connection portion 51 and the cable connection portion 53. The cable connection portion 53 is a protruded portion jutted out more outward than an outer shape of the image sensor 35. On the other hand, in the endoscope 15 according to the sixth modification, the pair of image sensors 35 are disposed with each of the cable connection portions 53 facing outward with the axis of the hard portion 25 sandwiched therebetween. That is, the cable connection portions 53 are separated outside. In a pair of sensor connection portions 51 sandwiched between the pair of separated cable connection portions 53, a surface on an opposite side of the image sensor 35 is covered with one shading member 97.

As in the fifth modification, in the endoscope 15, each of a pair of images captured by each of a pair of linked cameras 39 in which parallax is formed is processed, and a stereoscopic image in which depth information is reflected can be generated and displayed on the monitor 17.

The hard portion 25 of the endoscope 15 includes a pair of image capturing portions with the axis sandwiched therebetween. Each of the substrates connected to each of the image sensors 35 disposed in each of the pair of image capturing portions is formed by bending into an L shape with the sensor connection portion 51 parallel to the back surface of the image sensor 35 and the cable connection portion 53 perpendicular to the back surface, the pair of the image sensors 35 are disposed with each of the cable connection portions 53 facing outward with the axis of the hard portion 25 sandwiched therebetween, and a surface on an opposite side of the image sensor 35 of each of the sensor connection portion 51 connected to the back surface of each of the pair of image sensors 35 is covered with one shading member 97.

In the endoscope 15, since the cable connection portions 53 are separated outside, a pair of shading members 97 covering the pair of adjacent sensor connection portions 51 from the back surface side can be disposed on the inner side sandwiched between the pair of cable connection portions 53.

The image sensor 35 loaded on, for example, a blood vessel endoscope having an outer diameter of less than 1 mm is extremely thin in a square in which a length of a side is 0.5 mm or less. In this case, in order to improve handleability, the image sensor 35 is configured by attaching an image capturing surface to the sensor cover glass 57 having a length of a side of 0.5 mm and a thickness of 0.5 mm. The sensor cover glass 57 irradiates the image capturing surface of the image sensor 35 with image capturing light incident from the lens. At this time, a part of the image capturing light may leak from a side surface of the sensor cover glass 57 and may be incident from a back surface of the image sensor 35 which is thin due to action such as diffraction.

In the endoscope 15, illumination optical fibers which extend in an insertion direction and have a light emitting end disposed at a distal end in the insertion direction are disposed in parallel by sandwiching the image sensor 35. A part of the illumination light propagating through the optical fibers may leak out of cladding due to scattering or the like. In the endoscope 15, the shading member 97 reduces the leakage light from being incident (absorbed) from the back surface of the image sensor 35 and being photoelectrically converted into stray light. That is, the shading material 97 can collectively cover the back surfaces of the pair of image sensors 35 from visible light and infrared excitation light as stray light. In the endoscope 15 according to the sixth modification, by providing the voltage conversion device, the shading material 97 can be easily provided in the two-lens camera structure by effectively utilizing the space secured on the substrate.

Although various embodiments have been described above with reference to the drawings, it is needless to say that the present disclosure is not limited to such examples. It will be apparent to those skilled in the art that various changes, modifications, replacements, additions, deletions, equalizations can be conceived within the scope described in the claims, and it will be understood that those certainly belong to the technical scope of the present disclosure. Each constituent element in various embodiments mentioned above may be combined arbitrarily in a range that does not deviate from the spirit of the disclosure.

INDUSTRIAL APPLICABILITY

The present disclosure is useful as an endoscope in which an increase in diameter of a distal end portion can be reduced even though a transmission cable of a video signal obtained from an image capturing portion disposed at the distal end portion is long, and the image capturing portion can be stably operated at high resolution to obtain a high-resolution video signal.

What is claimed is:

1. An endoscope provided with a hard portion at a distal end of a scope, the endoscope comprising:
   an image capturing portion housed in the hard portion and having an image sensor;
   a substrate conductively connected to a transmission cable inserted into the scope and the image sensor; and
   a voltage conversion device mounted on the substrate and outputting a constant voltage to the image sensor with respect to an input voltage input to the transmission cable,
   wherein the substrate includes a first rigid substrate and a second rigid substrate connected by a hinge portion having flexibility, and
   the image sensor is mounted on the first rigid substrate, and the voltage conversion device is mounted on the second rigid substrate.

2. The endoscope according to claim 1, wherein the voltage conversion device is a linear regulator.

3. The endoscope according to claim 2, wherein the voltage conversion device is an LDO regulator.

4. The endoscope according to claim 1, wherein the voltage conversion device and the image sensor are mounted on the same flexible substrate.

5. The endoscope according to claim 1, wherein a wireless device is mounted on the substrate.

6. The endoscope according to claim 1, wherein a motor driving device is mounted on the substrate.

7. The endoscope according to claim 1, wherein the hard portion includes a pair of image capturing portions with an axis sandwiched therebetween,
   each of the substrates connected to each of the image sensors disposed in each of the pair of image capturing portions is formed by bending into an L-shape with a sensor connection portion parallel to a back surface of the corresponding image sensor and a cable connection portion perpendicular to the back surface, and
   each of the image sensors is disposed in a direction in which each of the cable connection portions faces each other with the axis of the hard portion sandwiched therebetween.

8. The endoscope according to claim 1, wherein the hard portion includes a pair of image capturing portions with an axis sandwiched therebetween,
   each of the substrates connected to each of the image sensors disposed in each of the pair of image capturing portions is formed by bending into an L-shape with a sensor connection portion parallel to a back surface of the corresponding image sensor and a cable connection portion perpendicular to the back surface,
   each of the image sensors is disposed with each of the cable connection portions facing outward with the axis of the hard portion sandwiched therebetween, and a surface on an opposite side of the image sensor of each of the sensor connection portion connected to the back surface of each of the pair of image sensors is covered with one shading member.

* * * * *